United States Patent [19]

Landsberger

[11] 4,367,203

[45] Jan. 4, 1983

[54] THERMAL SENSITIVE DEODORANT WAFER

[76] Inventor: David Landsberger, 60 Hibernia Rd., Rockaway, Morris County, N.J. 07866

[21] Appl. No.: 255,363

[22] Filed: Apr. 20, 1981

[51] Int. Cl.³ .............................................. A61L 9/12
[52] U.S. Cl. ........................................ 422/305; 422/5; 422/306; 55/279; 424/40; 424/76
[58] Field of Search .................... 55/279; 422/5, 121, 422/305, 306; 424/40, 76; 239/34, 53

[56] References Cited

U.S. PATENT DOCUMENTS

| 2,590,529 | 3/1952 | Gillies et al. | 424/40 |
| 2,603,532 | 7/1952 | Wheeler et al. | 422/5 |
| 3,274,758 | 9/1966 | Parman | 422/5 |
| 3,655,129 | 4/1972 | Seiner | 424/76 |
| 3,754,861 | 8/1973 | Sadahiro | 424/40 |
| 4,117,110 | 9/1978 | Hautmann | 424/76 |

FOREIGN PATENT DOCUMENTS 749811  5/1956  United Kingdom .

Primary Examiner—David L. Lacey
Attorney, Agent, or Firm—Anthony F. Cuoco

[57] ABSTRACT

A thermal sensitive deodorant wafer is disclosed which is used to neutralize odors caused by subjecting certain materials to elevated temperatures. A pad (2) is impregnated with a heat releasable deodorant and is encapsulated in a thermal sensitive shell (4) to form a wafer-like element (6). The shell decomposes when subjected to the elevated temperatures whereupon the deodorant is released to neutralize the odors.

3 Claims, 2 Drawing Figures

THERMAL SENSITIVE DEODORANT WAFER

BACKGROUND OF THE INVENTION

Offensive odors are experienced when certain materials are subjected to elevated temperatures. For example, such odors are experienced in laboratories and the like when biohazardous materials are autoclaved. Prior to the present invention, these odors were neutralized by pouring a liquid deodorant into the autoclave which often resulted in spillage. Moreover, storage facilities for the liquid deodorant are required and its use is otherwise inconvenient. Capsules containing liquid deodorants have been used but these present leakage and storage problems and are also otherwise inconvenient to use.

Accordingly, it is an object of the present invention to provide a convenient, easy to use deodorant wafer which eliminates the aforenoted disadvantages and is activated by the elevated temperatures which are responsible for the odors to be neutralized.

SUMMARY OF THE INVENTION

This invention contemplates a thermal sensitive deodorant wafer for the purposes described which includes a pad impregnated with a heat releasable essential oil deodorant. The pad is encapsulated in a thermal sensitive shell, whereby a wafer-like member is provided. The shell is of a material which decomposes when subjected to elevated temperatures, whereupon the essential oil deodorant is exposed to said temperatures and vaporizes to neutralize offensive odors caused thereby.

DETAILED DESCRIPTION OF THE INVENTION

A thin pad 2, which may be of a suitable, relatively absorbent material such as felt or the like, is impregnated with a heat releasable deodorant such as, for example, a heat releasable essential oil deodorant of the type which vaporizes at elevated temperatures. Such deodorants are commercially available and are known in the art.

Figure 1:
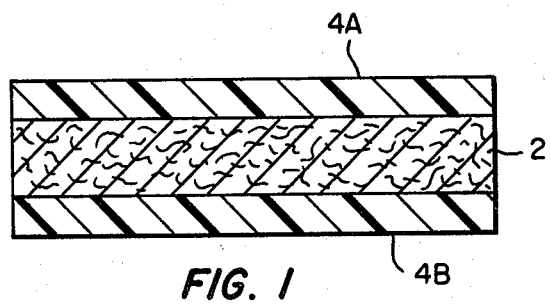
FIG. 1 is a sectional view showing a deodorant pad sandwiched between a pair of shell members according to the invention.

Pad 2 is sandwiched between a pair of thin shell members 4A and 4B as particularly shown in FIG. 1. Shell members 4A and 4B may be of a suitable plastic material which decomposes at elevated temperatures. By way of illustration, but not by way of limitation, this material may be a conventional polyethylene plastic.

Figure 2:
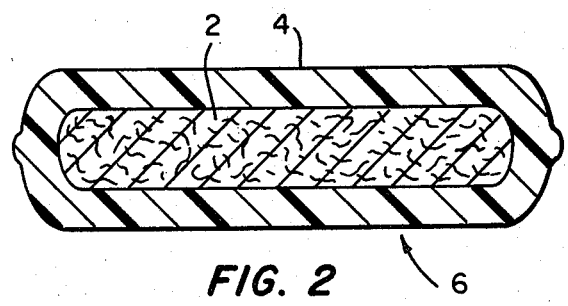
FIG. 2 is a sectional view showing the deodorant pad encapsulated within the shell members to form a wafer-like deodorant element according to the invention.

The sandwiched arrangement in FIG. 1 is subjected to appropriate temperature and pressure, whereby shell members 4A and 4B flow together so as to seal and encapsulate pad 2 within a thin walled continuous plastic shell 4 as shown in FIG. 2, and to thereby provide a wafer-like deodorant member designated by the numeral 6.

While the elements of the invention are enlarged in FIGS. 1 and 2 for purposes of describing the invention, it will be understood that the thickness of wafer 6 as particularly shown in FIG. 2 is about 0.050 inches. The wafer may be round, square, rectangular or any other shape suitable for the purposes intended. A typical round wafer has a diameter of about 1⅜ inches. It will also be understood that the size of the wafer may be larger or smaller than that described, depending on the purposes intended.

The amount of heat releasable essential oil deodorant impregnated on pad 2 may be measured so that the pad contains more or less of the deodorant substance commensurate with the intensity of the odor to be neutralized.

A typical use of the invention as described is during autoclaving of biohazardous materials or the like, which produces offensive odors. For this use, deodorant wafer 6 is dropped into the biohazardous material container and autoclaving is commenced.

A typical autoclaving temperature is about 240 degrees F. The material of shell 4 may be selected to decompose somewhat below this temperature or about 175 to 180 degrees F., whereupon the thin walled shell cracks, melts or otherwise decomposes to expose pad 2 to the autoclaving temperature. The heat releasable essential oil deodorant contained on pad 2 may be selected to vaporize at about this temperature, whereby the deodorant is released for neutralizing the offensive odor produced during autoclaving and leaves a mild pleasant residual scent. The invention as heretofore described obviates the disadvantages of other deodorant means for the purposes intended by eliminating spillage and/or leakage, and offers ease and convenience of use and storage so as to represent a distinct improvement in the art.

Having thus described the invention, what is claimed is:

1. A thermal sensitive deodorant wafer, comprising:
   a thermal sensitive thin walled shell;
   a pad impregnated with a heat releasable deodorant encapsulted within the shell, with the shell and the pad encapsulated therein providing the thermal sensitive deodorant wafer;
   the shell of the wafer being of a material sensitive to elevated temperatures for decomposing and exposing the pad when subjected to said temperatures; and
   the deodorant on the exposed pad being of a composition responsive to the elevated temperatures for being released from the pad and thereupon being effective for neutralizing offensive odors.

2. A thermal sensitive deodorant wafer as described by claim 1, wherein:
   the pad is of a relatively absorbent material; and
   the deodorant with which the pad is impregnated is an essential oil deodorant which vaporizes when the exposed pad is subjected to the elevated temperatures so as to be released from the pad and thereupon being effective for neutralizing offensive odors.

3. A thermal sensitive deodorant wafer for neutralizing offensive odors caused by subjecting certain substances to elevated temperatures, comprising:
   a relatively absorbent pad impregnated with an essential oil deodorant;
   a thin walled shell of a thermal sensitive material encapsulating the impregnated pad and forming therewith the thermal sensitive deodorant wafer;
   the thin walled shell being of a material sensitive to the elevated temperatures to which the certain substances are subjected so as to decompose when subjected to said temperatures, and to thereupon expose the pad encapsulated therein; and the essential oil deodorant with which the exposed pad is impregnated being of a composition responsive to the elevated temperatures for vaporizing so as to be released from the pad and thereupon neutralizing the offensive odors.

* * * * *